United States Patent
O'Rear et al.

(10) Patent No.: US 7,150,821 B2
(45) Date of Patent: Dec. 19, 2006

(54) HIGH PURITY OLEFINIC NAPHTHAS FOR THE PRODUCTION OF ETHYLENE AND PROPYLENE

(75) Inventors: Dennis J. O'Rear, Petaluma, CA (US); Guan Dao Lei, Walnut Creek, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 363 days.

(21) Appl. No.: 10/355,158

(22) Filed: Jan. 31, 2003

(65) Prior Publication Data

US 2004/0152933 A1    Aug. 5, 2004

(51) Int. Cl.
*C10G 9/00* (2006.01)
*C07C 1/04* (2006.01)

(52) U.S. Cl. ............... 208/106; 585/303; 585/302; 585/304; 585/329; 585/330

(58) Field of Classification Search ......... 208/950, 208/106; 585/303, 302, 304, 329, 330
See application file for complete search history.

(56) References Cited

U.S. PATENT DOCUMENTS

| | | | |
|---|---|---|---|
| 4,046,830 A * | 9/1977 | Kuo ............... | 208/64 |
| 4,125,566 A * | 11/1978 | Trin Dinh et al. ............ | 208/65 |
| 4,149,965 A | 4/1979 | Pine et al. | |
| 4,172,812 A | 10/1979 | Winter | |
| 4,172,843 A | 10/1979 | Dwyer et al. | |
| 4,207,250 A | 6/1980 | Butter et al. | |
| 4,269,783 A | 5/1981 | Brennan et al. | |
| 4,463,101 A | 7/1984 | Dwyer et al. | |
| 4,568,663 A | 2/1986 | Mauldin | |
| 4,645,586 A | 2/1987 | Buss | |
| 4,684,756 A * | 8/1987 | Derr et al. ............... | 585/330 |
| 5,322,615 A | 6/1994 | Holtermann et al. | |
| 5,371,308 A | 12/1994 | Gosselink et al. | |
| 5,506,272 A | 4/1996 | Benham et al. | |
| 5,689,031 A | 11/1997 | Berlowitz et al. | |
| 5,766,274 A | 6/1998 | Wittenbrink et al. | |
| 6,069,287 A * | 5/2000 | Ladwig et al. ............ | 585/648 |
| 6,162,956 A | 12/2000 | Berlowitz et al. | |
| 6,180,842 B1 | 1/2001 | Berlowitz et al. | |
| 6,274,029 B1 | 8/2001 | Wittenbrink et al. | |
| 6,296,757 B1 | 10/2001 | Wittenbrink et al. | |

(Continued)

FOREIGN PATENT DOCUMENTS

EP    0361681    4/1990

(Continued)

OTHER PUBLICATIONS

Jack Owen, "Conversion and uses of liquid fuels from coal", Coal Research Establishment, National Coal Board, Stoke Orchard, Cheltenham, Glos, GL52 4RZ, UK.

(Continued)

*Primary Examiner*—Tam M. Nguyen
(74) *Attorney, Agent, or Firm*—Buchanan, Ingersoll & Rooney PC (57) ABSTRACT

The present invention relates to an olefinic naphtha and a process for producing lower olefins from this naphtha. In the process of the present invention for producing lower olefins, preferably ethylene, at least a portion of a hydrocarbon asset is converted to synthesis gas and at least a portion of the synthesis gas is converted to an olefinic naphtha by a Fischer-Tropsch process. At least a portion of the olefinic naphtha is converted in a naphtha cracker to a product stream comprising lower olefins, and at least a portion of the lower olefins from the product stream of the naphtha cracker are recovered.

27 Claims, 1 Drawing Sheet

U.S. PATENT DOCUMENTS

| | | | |
|---|---|---|---|
| 6,369,286 B1 | 4/2002 | O'Rear | |
| 6,455,750 B1* | 9/2002 | Steffens et al. | 585/648 |
| 6,605,206 B1 | 8/2003 | Johnson et al. | |
| 6,703,535 B1* | 3/2004 | Johnson et al. | 585/303 |
| 6,743,962 B1 | 6/2004 | O'Rear et al. | |
| 6,900,366 B1* | 5/2005 | Rosenbaum et al. | 585/821 |
| 2003/0199719 A1 | 10/2003 | Johnson et al. | |

FOREIGN PATENT DOCUMENTS

| | | |
|---|---|---|
| EP | 0609079 A1 | 1/1994 |
| EP | 0161705 | 11/1995 |
| EP | 0921179 A1 | 6/1999 |
| GB | 816540 | 7/1959 |
| GB | 879506 | 10/1961 |
| GB | 2 371 807 | 8/2002 |
| WO | 97/14769 | 4/1997 |
| WO | 98/56740 | 12/1998 |
| WO | 98/56873 | 12/1998 |
| WO | 98/56877 | 12/1998 |
| WO | 00/18853 | 4/2000 |
| WO | 00/60029 | 10/2000 |
| WO | 01/34731 | 5/2001 |
| WO | 02/094426 | 11/2002 |
| WO | 2004/067486 | 8/2004 |

OTHER PUBLICATIONS

"Ethylene from Mobil Zeolite and F-T route economic by 1990", ECN Technolgoy, p. 16.

"Coal-Based chemicals complex outlined", C&EN, Sep. 6, 1976, p. 7.

H. M. Hutcheon, "Conference: Industrial Conversion of Coal and Carbon to Gas, Liquid and High-Value Sold Products", Organized by the INdustrial Carbon and Grphite Goup of the Society of Chemical Industry, held at the Society of Chemical Industry, London, Apr. 7-8, 1981.

Lewis F. Hatch and Sami Matar, "From Hydrocarbons to Petrochemicals . . . ", Phoenix, Mar. 1978, pp. 128-139.

A.G.Goossens, "Prediction of Molecular Weight of Petroleum Fractions", IEC Res. 1996, 35, p. 985-988.

"Ethylene", Encyclopedia of Chemical Technology, Ed. 4, New York; vol. 9, pp. 877-915.

Adriaan G. Goossens, "Prediction of Molecular Weight of Petroleum Fractions", Ind. Eng. Chem., Res, 1996, 35, pp. 985-988.

Dr. Richard A. White, "Materials Selection for Petroleum Refineries and Gathering Facilities", NACE International, 1998, Houston, TX pp. 1-14.

Shah, P.P., "Upgrading of Light Fischer-Tropsch Products, Final Report", U.S. Dept. of Energy, DE91011315, Nov. 30, 1990.

United Kingdom Search Report dated Jun. 30, 2004.

U.S. Appl. No. 10/043,345, O'Rear et al., filed Jan. 14, 2002, "Olefin Production from Low Sulfur Hydrocarbon Fractions."

U.S. Appl. No. 10/355,280, O'Rear et al., filed Jan. 31, 2003, "Stable Olefinic, Low Sulfur Diesel Fuels."

Chevron Corporation, *Technical Review Diesel Fuels*, Chapter 7 Diesel Fuel Additives, pp. 55-61 (1998).

Dancuar, L.P., et al., "Performance of the Sasol SPD Naphtha as Steam Cracking Feedstock",*Petroleum Chemistry Division Preprints* 48(2): 132-138 (2003).

Sundaram, K.M, et al., "Ethylene", *Kirk-Othmer Encyclopedia of Chemical Technology*, Chapter 4, Apr. 16, 2001.

Schlesinger, M.D. and H. E. Benson, "Upgrading Fischer-Tropsch Products", *Industrial and Engineering Chemistry* 47(10):2104-2108 (1954).

United Kingdom Search Reports, one dated Jan. 17, 2005 and two dated Jan. 18, 2005.

Netherlands search report dated Feb. 23, 2005.

International Search Report dated May 30, 2005.

Shah, P.P., "Upgrading of Light Fischer-Tropsch Products, Final Report" Contract No. AC22-86PC90014. DE91011315 (DOE/PC/90014-TB)(1990).

Vardi J. et al. "Peroxide Formation in Low Sulfur Automotive Diesel Fuels" SAE paper 920826 (1992).

Technical Review Diesel Fuels, *J. Diesel Fuel Refining and Chemistry*, Chevron Products Company, no date.

U.S. Appl. No. 10/354,957, O'Rear et al., filed Jan. 31, 2003, High Purity Olefinic Naphthas from the Production of Ethylene and Propylene.

U.S. Appl. No. 10/355,110, Lei et al., filed Jan. 31, 2003, High Purity Olefinic Naphthas from the Production of Ethylene and Propylene.

U.S. Appl. No. 10/355,279, O'Rear et al., filed Jan. 31, 2003, "Low Acid, High Olefin Fischer-Tropsch Distillate Fuel".

U.S. Appl. No. 10/354,956, O'Rear et al., filed Jan. 31, 2003, "Low Acid, High Olefin Fischer-Tropsch Distillate Fuel".

U.S. Appl. No. 10/358,129, filed Jan. 31, 2003, Sasol Technology (Pty) Ltd. "Process for the Preparation of and Composition of a Feedstock Usable for the Preparation of Lower Olefins".

* cited by examiner

Figure

HIGH PURITY OLEFINIC NAPHTHAS FOR THE PRODUCTION OF ETHYLENE AND PROPYLENE

CROSS-RELATED APPLICATIONS

The present application is related to U.S. patent application Ser. No. 10/355,110 entitled "High Purity Olefinic Naphthas for the Production of Ethylene and Propylene" and U.S. patent application Ser. No. 10/354,957 now U.S. Pat. No. 6,872,752 entitled "High Purity Olefinic Naphthas for the Production of Ethylene and Propylene" both of which are filed herewith.

FIELD OF THE INVENTION

This invention relates to improved techniques for producing lower olefins from high purity olefinic naphthas. More specifically, the invention relates to a process for converting an inexpensive hydrocarbon resource from a remote location into high purity olefinic naphtha, transporting the olefinic naphtha to a second facility, and subsequently processing the olefinic naphtha to produce lower olefins.

BACKGROUND OF THE INVENTION

Lower olefins, in particular olefins having from 2 to 4 carbon atoms, are suitable starting materials in a large number of chemical processes, including, for example, alkylation, oligomerization, and polymerization processes. The preparation of lower olefins from a hydrocarbon feed by cracking of that feed is a well-known process and is commercially applied at a large number of petrochemical manufacturing facilities. Typically, a distillate fraction of a crude oil, commonly a naphtha fraction of the crude oil, is used as the hydrocarbon feed in a naphtha cracker process to produce ethylene.

For commercial reasons, there is a demand for a naphtha cracking process having a high selectivity for lower olefins, in particular ethylene. There is also a demand to manufacture ethylene from hydrocarbon assets other than petroleum naphthas, especially ones that cost less and are more abundant. Examples of such hydrocarbon assets include natural gas, coal, and heavy oils found in abundant supply in locations that are remote from the ethylene markets. Currently there are two approaches to converting remote hydrocarbon assets into ethylene where the ethylene is manufactured in developed locations.

The first approach is to convert a hydrocarbon asset obtained at a remote site into a highly paraffinic feed by a Fischer-Tropsch process. This approach involves converting the hydrocarbon asset into synthesis gas by partial oxidation and converting the synthesis gas into a mixture of hydrocarbons by a Fischer-Tropsch process. A hydrocarbon fraction from the Fischer-Tropsch process may be used as a feed to a naphtha cracking process to produce ethylene. By way of example, European Patent Application No. 161705 discloses that a fraction of the product of a Fischer-Tropsch synthesis process may be used as a hydrocarbon feed in a naphtha cracking process. EP 161705 discloses using a $C_{19-}$ fraction from the Fischer-Tropsch process, wherein the $C_{19-}$ fraction substantially consists of linear paraffins, as a feed for a naphtha cracking process. EP 161705 further discloses that by using this feed, the selectivity toward lower olefins is increased compared with a naphtha fraction of a crude oil.

To increase the selectivity of the naphtha cracking process, a highly paraffinic Fischer-Tropsch naphtha that has been processed using hydrogen, including hydrotreating, hydrocracking, and hydroisomerization is typically used. To produce the ethylene, the highly paraffinic Fischer-Tropsch naphtha is typically shipped from the site where synthesized to a developed site and converted into ethylene in a naphtha cracker.

By way of example, "Performance of the SASOL SPD Naphtha as Steam Cracking Feedstock", by Luis P. Dancuart, et al., ACS 2002 National Meeting, Boston Mass, Aug. 18–22, 2002, ACS Preprints Jul. 2002, and U.S. Pat. No. 5,371,308 describe examples of this approach. U.S. Pat. No. 5,371,308 teaches a process for preparing lower olefins from a hydrocarbon feed comprising a hydroprocessed synthetic oil fraction, wherein the hydrocarbon feed comprising the hydroprocessed synthetic oil fraction is cracked. The hydroprocessed synthetic oil fraction is derived from a synthesis process, such as a Fischer-Tropsch synthesis process and is subsequently treated in a process in the presence of hydrogen.

The second approach for converting a remote hydrocarbon asset into ethylene involves the production of methanol. This approach involves converting the hydrocarbon asset obtained at a remote site into synthesis gas by partial oxidation and converting the synthesis gas in a methanol synthesis plant into methanol. The methanol is typically shipped to a developed site and converted into ethylene by a Methanol-to-Olefins process. The methanol to olefins process uses a molecular sieve to dehydrate and convert the methanol to a mixture of ethylene, propylene and other olefins.

There are advantages to using the process involving Fischer-Tropsch naphtha to produce ethylene in comparison to the methanol process. These advantages include that the process involving Fischer-Tropsch naphtha can use existing conventional naphtha crackers. Also, the highly paraffinic naphtha produced in this process consists of a mixture of normal and iso-paraffins with few cyclic compounds (aromatics and naphthenes). This highly paraffinic naphtha provides higher yields of ethylene and lower coking rates than typical petroleum naphthas.

However, there are certain disadvantages of the process involving use of Fischer-Tropsch naphtha. The disadvantages include the high cost of converting methane into highly paraffinic naphtha. One element of this high cost is the hydrogen that is typically needed to hydrotreat the Fischer-Tropsch products to provide the highly paraffinic naphtha. In addition, the ethylene cracking step involves a high temperature endothermic reaction to dehydrogenate and crack the naphtha into smaller fragments. This high temperature endothermic reaction require the use of a significant amount of costly fuel.

The approach involving methanol synthesis may require fewer steps, but in general the economics of methanol production from natural gas are poor. In addition, when methanol is shipped, it must be remembered that approximately 50 wt % of the methanol is converted into water during the Methanol-to-Olefins step. Thus, approximately twice the amount of methanol must be shipped in comparison to a paraffinic naphtha. Furthermore, since methanol is toxic, it is typically shipped in small specialty tankers at higher costs than those needed for paraffinic naphthas. Finally, this approach requires the construction of new facilities for the Methanol-to-Olefins step.

There is a demand for economical and efficient processes to convert inexpensive hydrocarbon assets (such as methane or coal from remote sites) to ethylene in developed locations. It is desired that these processes have certain advantages. It is desired that the initial conversion of the hydrocarbon asset to the feed for the naphtha cracker be economical. It is desirable that the feed give high yields of ethylene thus requiring a smaller amount of feed initially. It is desirable that the naphtha cracking step have low operating costs. It is desirable that the overall process be compatible with existing facilities, including, for example, ships, tanks, pumps, naphtha crackers, etc.

SUMMARY OF THE INVENTION

The present invention relates to techniques for producing lower olefins from high purity olefinic naphthas. In one aspect the present invention relates to a process for producing lower olefins. The process comprises converting at least a portion of a hydrocarbon asset to synthesis gas, and converting at least a portion of the synthesis gas to an olefinic naphtha by a Fischer-Tropsch process. At least a portion of the olefinic naphtha is converted in a naphtha cracker to a product stream comprising lower olefins, and at least a portion of the low olefins from the produce stream of the naphtha cracker are recovered.

In another aspect the present invention relates to a process for producing ethylene. The process comprises converting at least a portion of a hydrocarbon asset to synthesis gas, and converting at least a portion of the synthesis gas to a hydrocarbon stream in a Fischer-Tropsch process unit. An olefinic naphtha from the hydrocarbon stream is isolated, wherein the olefinic naphtha comprises 25 to 80 weight % olefins and 20 to 75 weight % non-olefins, wherein the non-olefins comprise greater than 75 weight % paraffins. The olefinic naphtha is purified in the presence of a metal oxide to provide a purified olefinic naphtha having a total acid number of less than 1.5, and at least a portion of the purified olefinic naphtha is converted in a naphtha cracker to a product stream comprising ethylene. At least a portion of the ethylene from the product stream of the naphtha cracker is recovered.

In a further aspect, the present invention relates to a process for manufacturing ethylene including a first site and a second site, remote from each other, wherein the first site forms an olefinic Fischer-Tropsch naphtha to be used at the second site, the second site forming the ethylene. The process comprises receiving at the second site the olefinic Fischer-Tropsch naphtha, converting the olefinic naphtha in a naphtha cracker to a product stream comprising ethylene, and isolating ethylene from the product stream of the naphtha cracker. In this process the olefinic Fischer-Tropsch naphtha is made by a process comprising converting a hydrocarbon asset to syngas, subjecting the syngas to Fischer-Tropsch synthesis to form hydrocarbonaceous products, and isolating the olefinic Fischer-Tropsch naphtha from the hydrocarbonaceous products.

In yet another aspect, the present invention relates to an olefinic naphtha. The olefinic naphtha comprises (a) olefins in an amount of 10 to 80 weight %, (b) non-olefins in an amount of 20 to 90 weight %, wherein the non-olefins comprise greater than 50 weight % paraffins, (c) sulfur in an amount of less than 10 ppm by weight, (d) nitrogen in an amount of less than 10 ppm by weight, (e) aromatics in an amount less than 10 weight %, (f) a total acid number of less 1.5, and (g) a boiling range of $C_5$ to 400° F.

The present invention also relates to an olefinic naphtha comprising (a) olefins in an amount of 25 to 80 weight %, wherein the olefins are comprised of greater than 65 weight % linear primary olefins, (b) non-olefins in an amount of 20 to 75 weight %, wherein the non-olefins comprise greater than 75 weight % paraffins and the paraffins have an i/n ratio of less than 1, (c) sulfur in an amount of less than 2 ppm by weight, (d) nitrogen in an amount of less than 2 ppm by weight, (e) aromatics in an amount less than 2 weight %, (f) a total acid number of less 1.5, and (g) a boiling range of $C_5$ to 400° F.

In another aspect, the present invention relates to a process of producing an olefinic naphtha. The process comprises converting at least a portion of a hydrocarbon asset to synthesis gas, and converting at least a portion of the synthesis gas to a hydrocarbon stream in a Fischer-Tropsch process unit. An olefinic naphtha is isolated from the hydrocarbon stream, wherein the olefinic naphtha comprises 10 to 80 weight % olefins and 20 to 90 weight % non-olefins, wherein the non-olefins comprise greater than 50 weight % paraffins. The olefinic naphtha is purified by contacting the olefinic naphtha with a metal oxide at elevated temperatures, and a purified olefinic naphtha having a total acid number of less than 1.5 is isolated.

In yet another aspect, the present invention relates to a blended naphtha. The blended naphtha comprises (a) an olefinic naphtha comprising 10 to 80 weight % olefins and 20 to 90 weight % non-olefins, wherein the non-olefins comprise greater than 50 weight % paraffins and (b) a naphtha selected from the group consisting of a hydrotreated Fischer-Tropsch derived naphtha, a hydrocracked Fischer-Tropsch derived naphtha, a hydrotreated petroleum derived naphtha, a hydrocracked petroleum derived naphtha, and mixtures thereof. The blended naphtha comprises less than 10 ppm sulfur and has an acid number of less than 1.5.

In a further aspect, the present invention relates to a process for producing a blended naphtha. The process comprises converting at least a portion of a hydrocarbon asset to synthesis gas and converting at least a portion of the synthesis gas to a hydrocarbon stream in a Fischer-Tropsch reactor. An olefinic naphtha is isolated wherein the olefinic naphtha comprises 10 to 80 weight % olefins and 20 to 90 weight % non-olefins, wherein the non-olefins comprise greater than 50 weight % paraffins. The olefinic naphtha is mixed with a naphtha selected from the group consisting of a hydrocracked Fischer-Tropsch derived naphtha, a hydrotreated Fischer-Tropsch derived naphtha, a hydrocracked petroleum derived naphtha, a hydrotreated petroleum derived naphtha, and mixtures thereof to provide a blended naphtha. The blended naphtha comprises less than 10 ppm sulfur and has an acid number of less than 1.5.

In yet a further aspect, the present invention relates to a process for producing a blended naphtha. The process comprises providing an olefinic naphtha comprising 10 to 80 weight % olefins and 20 to 90 weight % non-olefins, wherein the non-olefins comprise greater than 50 weight % paraffins. The olefinic naphtha is mixed with a naphtha selected from the group consisting of a hydrocracked Fischer-Tropsch derived naphtha, a hydrotreated Fischer-Tropsch derived naphtha, a hydrocracked petroleum derived naphtha, a hydrotreated petroleum derived naphtha, and mixtures thereof to provide a blended naphtha. The blended naphtha comprises less than 10 ppm sulfur and has an acid number of less than 1.5.

DETAILED DESCRIPTION OF THE ILLUSTRATIVE EMBODIMENTS

The present invention relates to an olefinic naphtha and a process for producing lower olefins from this olefinic naphtha.

Definitions

The following terms will be used throughout the specification and will have the following meanings unless otherwise indicated.

The term "naphtha" means a hydrocarbonaceous mixture containing compounds boiling between $C_5$ and 400° F. The $C_5$ analysis is performed by gas chromatography, and the 400° F. temperature refers to the 95% boiling point as measured by ASTM D-2887. Preferably, at least 65% of the hydrocarbonaceous mixture boils between $C_5$ and 400° F., most preferably at least 85%.

The term "paraffin" means a saturated straight or branched chain hydrocarbon (i.e., an alkane).

The term "olefins" means an unsaturated straight or branched chain hydrocarbon having at least one double bond (i.e., an alkene).

The term "olefinic naphtha" means a naphtha containing 10 to 80 wt % olefins and 20 to 90 wt % non-olefins, wherein the non-olefins contain predominantly paraffins. Preferably, olefinic naphtha contains greater than or equal to 25 to 80 wt % olefins, and more preferably 50 to 80 wt % olefins. Preferably the non-olefins of the olefinic naphtha comprise greater than 50 wt % paraffins, more preferably greater than 75 wt % paraffins, and even more preferably greater than 90 wt % paraffins (weight % are based on the non-olefin component). Preferably, the olefinic naphtha also contains less than 10 ppm sulfur and less than 10 ppm nitrogen, and more preferably both sulfur and nitrogen are less than 5 ppm, more preferably less than 2 ppm, and even more preferably less than 1 ppm. Preferably the olefinic naphtha contains less than 10 wt % aromatics, more preferably less than 5 wt % aromatics, and even more preferably less than 2 wt % aromatics. Olefins and aromatics are preferably measured by SCFC (Supercritical Fluid Chromatography).

The term "lower olefins" means olefins having from 2 to 4 carbons. Preferably lower olefins refer to ethylene and propylene, more preferably ethylene.

The term "linear primary olefins" means a straight chain 1-alkene, commonly known as alpha olefins.

The term "total acid number" or "acid value" is a measurement of acidity. It is determined by the number of milligrams of potassium hydroxide required for the neutralization of acids present in 1 gram of the sample being measured (mg KOH/g), as measured by ASTM D 664 or a suitable equivalent. The olefinic naphtha used in the processes of the present invention preferably have a total acid number of less than 1.5 mg KOH/g and more preferably less than 0.5 mg KOH/g.

The term "oxygenates" means a hydrocarbon containing oxygen, i.e., an oxygenated hydrocarbon. Oxygenates include alcohols, ethers, carboxylic acids, esters, ketones, and aldehydes, and the like.

The term "i/n ratio" means isoparaffin/normal paraffin weight ratio. It is the ratio of the total number of iso-paraffins (i.e., branched) to the total number of normal-paraffins (i.e., straight chain) in a given sample.

The term "derived from a Fischer-Tropsch process" or "Fischer-Tropsch derived" means that the product, fraction, or feed originates from or is produced at some stage by a Fischer-Tropsch process.

The term "derived from a petroleum" or "petroleum derived" means that the product, fraction, or feed originates from the vapor overhead streams from distilling petroleum crude and the residual fuels that are the non-vaporizable remaining portion. A source of the petroleum-derived can be from a gas field condensate.

The term "hydrotreated Fischer-Tropsch derived naphtha" means a naphtha that is derived from hydrotreating a $C_5$ to 400° F. containing Fischer-Tropsch product.

The term "hydrocracked Fischer-Tropsch derived naphtha" means a naphtha that is derived from hydrocracking a 400° F.+ containing Fischer-Tropsch product.

The term "hydrocracked petroleum derived naphtha" means a naphtha that is derived from hydrocracking 400° F.+ containing petroleum derived products.

The term "hydrotreated petroleum derived naphtha" means a naphtha that is derived from hydrotreating a $C_5$ to 400° F. containing petroleum derived product.

The term "elevated temperature" means temperatures greater than 20° C. In the process of the present invention, elevated temperatures, with reference to the purification of the olefinic naphthas, are preferably greater than 450° F.

It has been surprisingly discovered that an olefinic naphtha produced from a Fischer-Tropsch process, rather than a paraffinic naphtha, provides certain advantages. For example, the costs associated with producing the olefinic naphtha are reduced because a hydroprocessing step, and thus expensive hydrogen, is not required to manufacture the olefinic naphtha. In addition, when the olefinic naphtha is used to make lower olefins, for example ethylene, the yields of ethylene are increased because olefins provide higher ethylene yields than paraffins. Therefore, the amount of feed to a naphtha cracker to produce a desired quantity of ethylene is less when using an olefin feed in comparison to a paraffin feed. Furthermore, the operating costs for the naphtha cracker are reduced because the heat of conversion requirements of olefins to ethylene are less than for the corresponding paraffins. Moreover, existing facilities, such as ships, tanks, pumps, naphtha crackers, etc, can be used when manufacturing an olefinic naphtha and lower olefins from the olefinic naphtha.

Accordingly, the present invention relates to an olefinic naphtha. The olefinic naphtha of the present invention is made by a Fischer-Tropsch process.

In the Fischer-Tropsch synthesis process, liquid and gaseous hydrocarbons are formed by contacting a synthesis gas (syngas) comprising a mixture of $H_2$ and CO with a Fischer-Tropsch catalyst under suitable temperature and pressure reactive conditions. The Fischer-Tropsch reaction is typically conducted at temperatures of about from 300 to 700° F. (149 to 371° C.) preferably about from 400° to 550° F. (204° to 228° C.); pressures of about from 10 to 600 psia, (0.7 to 41 bars) preferably 30 to 300 psia, (2 to 21 bars) and catalyst space velocities of about from 100 to 10,000 cc/g/hr., preferably 300 to 3,000 cc/g/hr.

The products may range from $C_1$ to $C_{200+}$ with a majority in the $C_5$–$C_{100+}$ range. The reaction can be conducted in a variety of reactor types for example, fixed bed reactors containing one or more catalyst beds, slurry reactors, fluidized bed reactors, or a combination of different type reactors. Such reaction processes and reactors are well known and documented in the literature. Slurry Fischer-Tropsch processes, which is a preferred process in the practice of the invention, utilize superior heat (and mass) transfer characteristics for the strongly exothermic synthesis reaction and are able to produce relatively high molecular weight, paraffinic hydrocarbons when using a cobalt catalyst. In a slurry process, a syngas comprising a mixture of $H_2$ and CO is bubbled up as a third phase through a slurry in a reactor which comprises a particulate Fischer-Tropsch type hydrocarbon synthesis catalyst dispersed and suspended in a slurry liquid comprising hydrocarbon products of the synthesis reaction which are liquid at the reaction conditions. The mole ratio of the hydrogen to the carbon monoxide may broadly range from about 0.5 to 4, but is more typically within the range of from about 0.7 to 2.75 and preferably from about 0.7 to 2.5. A particularly preferred Fischer-Tropsch process is taught in EP0609079.

Suitable Fischer-Tropsch catalysts comprise on or more Group VIII catalytic metals such as Fe, Ni, Co, Ru and Re. Additionally, a suitable catalyst may contain a promoter. Thus, a preferred Fischer-Tropsch catalyst comprises effective amounts of cobalt and one or more of Re, Ru, Pt, Fe, Ni, Th, Zr, Hf, U, Mg and La on a suitable inorganic support material, preferably one which comprises one or more refractory metal oxides. In general, the amount of cobalt present in the catalyst is between about 1 and about 50 weight percent of the total catalyst composition. The catalysts can also contain basic oxide promoters such as $ThO_2$, $La_2O_3$, MgO, and $TiO_2$, promoters such as $ZrO_2$, noble metals (Pt, Pd, Ru, Rh, Os, Ir), coinage metals (Cu, Ag, Au), and other transition metals such as Fe, Mn, Ni, and Re. Support materials including alumina, silica, magnesia and titania or mixtures thereof may be used. Preferred supports for cobalt containing catalysts comprise titania. Useful catalysts and their preparation are known and illustrative, but nonlimiting examples may be found, for example, in U.S. Pat. No. 4,568,663.

The products from Fischer-Tropsch reactions performed in slurry bed reactors generally include a light reaction product and a waxy reaction product. The light reaction product (i.e. the condensate fraction) includes hydrocarbons boiling below about 700° F. (e.g., tail gases through middle distillates), largely in the $C_5$–$C_{20}$ range, with decreasing amounts up to about $C_{30}$. The waxy reaction product (i.e. the wax fraction) includes hydrocarbons boiling above about 600° F. (e.g., vacuum gas oil through heavy paraffins), largely in the $C_{20+}$ range, with decreasing amounts down to $C_{10}$. Both the light reaction product and the waxy product are substantially paraffinic. The waxy product generally comprises greater than 70% normal paraffins, and often greater than 80% normal paraffins. The light reaction product comprises paraffinic products with a significant proportion of alcohols and olefins. In some cases, the light reaction product may comprise as much as 50%, and even higher, alcohols and olefins.

The olefinic naphtha of the present invention may be isolated from the products of the products of the Fischer-Tropsch process by distillation. The olefinic naphtha of the present invention boils between $C_5$ to 400° F.

In the process of the present invention, the olefinic naphtha may be purified. Olefinic naphtha from Fischer-Tropsch facilities frequently contain impurities that should be removed, but without saturation of the olefins. Examples of these impurities include acids and heavy metals. The acids present in Fischer-Tropsch naphthas are corrosive and will rapidly attack metal surfaces in ships, tanks, pumps, and the naphtha cracker. Since the acids attack metals, the metals will become incorporated into the naphtha and lead to increased fouling of furnace tubes in downstream processors, including for example, a naphtha cracker. In addition, metals can be incorporated into the naphtha by direct reaction of the acids with typical Fischer-Tropsch catalysts—e.g. iron. Therefore, it may be necessary to remove the acids and dissolved metals present in the olefinic naphtha by a process that can do so without saturating the olefins.

Alcohols and other oxygenates may also be present in the olefinic naphtha from the Fischer-Tropsch facility. While alcohols and other oxygenates can be handled in a naphtha cracker, it can be desirable to remove them as well as the dissolved metals and acids.

In processing conventional petroleum, it is standard that crude oils should have total acid numbers less than 0.5 mg KOH/g in order to avoid corrosion problem. It is further standard that distillate fractions have acid numbers less than 1.5 mg KOH/g. See, "Materials Selection for Petroleum Refineries and Gathering Facilities", Richard A. White, NACE International, 1998 Houston Tex. pages 6–9.

Therefore, the purification processes of the present invention for the olefinic naphtha are capable of providing an olefinic naphtha with a total acid number preferably less than 1.5 mg KOH/g, more preferably less than 1.0 mg KOH/g, and even more preferably less than 0.5 mg KOH/g, without appreciably saturating the olefins contained therein. The olefinic naphtha isolated directly from the Fischer-Tropsch process may have an acceptable total acid number. However, if the olefinic naphtha isolated does not have an acceptable total acid number, it will be necessary to purify it as described herein.

In the conventional technology that produces a highly paraffinic naphtha, impurities, including acids, alcohols, and other oxygenates, are removed by a hydroprocessing technique, for example, hydrotreating, hydrocracking, hydroisomerization etc. However, these processes also simultaneously convert the desirable olefins into relatively less desirable paraffins.

According to the present invention, the acids and dissolved metals in Fischer-Tropsch naphthas are removed by contacting the naphtha with a metal oxide catalyst at elevated temperatures. In contacting the naphtha with the metal oxide at elevated temperatures, acids are converted into paraffins and olefins by decarboxylation. In addition, alcohols are converted into additional olefins by dehydration, and other oxygenates (including ethers, esters, and aldehydes found at relatively smaller amounts) are converted into hydrocarbons. In this process for purification of naphtha, expensive hydrogen is not needed; however, it can be used if desired (to improve catalyst/naphtha contacting or for heat control). The oxygen in the naphtha is converted into water and carbon dioxide, which can easily be separated from the product olefinic naphtha.

If dissolved metals are present in the naphtha, they will be simultaneously removed and deposited on the metal oxide catalyst. Typically, the metal oxide catalysts used in the purification process according to the present invention will show low deactivation rates; however, eventually the catalysts will need to be regenerated or replaced. Regeneration of the catalysts can be accomplished by stripping with a high temperature gas (hydrogen or other), or by burning the catalyst while it is in contact with an oxygen containing gas at elevated temperatures. Regeneration by burning is preferred.

Preferably the purification according to the present invention is performed by passing the olefinic naphtha through a purification unit containing a metal oxide under conditions of 450 to 800° F., less than 1000 psig, and 0.25 to 10 LHSV without added gaseous components. By way of example, the purification process may be performed by passing the olefinic naphtha downflow through a purification unit containing a metal oxide at elevated temperatures.

Preferably, the metal oxide is selected from the group consisting of alumina, silica, silica-alumina, zeolites, clays, and mixtures thereof. Since terminal olefins are believed to give the highest yield of ethylene, it is preferable to select an oxide that is effective for dehydration of the oxygenates, yet does not promote isomerization of the olefins from their terminal position to internal or branched olefins. On this basis, a preferred metal oxide is alumina. Additional components can be added to the metal oxide to promote the dehydration or retard olefin isomerization. Examples of such additional components are basic elements such as Group I or II elements of the periodic table. These basic components can also retard catalyst fouling. Usually these components are incorporated into the oxide form in the finished catalyst.

The severity of the purification process can be varied as necessary to achieve the desired total acid number. Typically the severity of the process is varied by adjusting the temperature, and LHSV. Accordingly, a more severe purification may be accomplished by running the purification process at a higher temperature, and under these more severe purification conditions more oxygenates will be removed, thus providing an olefinic naphtha with a lower total acid number.

The purification processes of the present invention provide an olefinic naphtha with a total acid number preferably less than 1.5 mg KOH/g, more preferably less than 1.0 mg KOH/g, and even more preferably less than 0.5 mg KOH/g, without saturating the olefins contained therein. The purification processes of the present invention preferably remove more than 80 weight percent of the oxygenates in the olefinic naphtha.

The olefinic naphtha according to the present invention is a naphtha containing 10 to 80 wt % olefins and 20 to 90 wt % non-olefins, wherein the non-olefins contain predominantly paraffins. Preferably, olefinic naphtha contains greater than or equal to 25 to 80 wt % olefins, and more preferably 50 to 80 wt % olefins. The olefins of the olefinic naphtha are predominantly linear primary olefins. Preferably, the olefins comprise greater than 50 wt % linear primary olefins, more preferably greater than 65 wt % linear primary olefins, and even more preferably greater than 80 wt % linear primary olefins.

The non-olefinic component of the olefinic naphtha is predominantly paraffinic. Preferably the non-olefins comprise greater than 50 wt % paraffins, more preferably greater than 75 wt % paraffins, and even more preferably greater than 90 wt % paraffins (as measured on the basis of the non-olefinic component). The paraffins of the non-olefinic component of the naphtha are predominantly n-paraffins. Preferably the paraffins have an i/n ratio of less than 1.0 and more preferably less than 0.5.

In addition, preferably, the olefinic naphtha also contains less than 10 ppm sulfur and less than 10 ppm nitrogen, and more preferably both sulfur and nitrogen are less than 5 ppm, more preferably less than 2 ppm, and even more preferably less and 1 ppm. Furthermore, the olefinic naphtha preferably contains less than 10 wt % aromatics, more preferably less than 5 wt % aromatics, and even more preferably less than 2 wt % aromatics. Olefins and aromatics are preferably measured by SCFC (Supercritical Fluid Chromatography).

The olefinic naphtha according to the present invention may be blended to provide a blended naphtha. This blended naphtha may be used for any purpose for which a naphtha is used. These purposes include processes for producing ethylene, including both traditional processes and the process of the present invention. A blended naphtha comprises the olefinic naphtha as described above and a naphtha selected from the group consisting of a hydrotreated Fischer-Tropsch derived naphtha, a hydrocracked Fischer-Tropsch naphtha, a hydrotreated petroleum derived naphtha, a hydrocracked petroleum derived naphtha, and mixtures thereof. The blended olefinic naphtha according to the present invention is made by a process comprising mixing an appropriate amount of an olefinic naphtha, as described herein, with another naphtha selected from the group, as defined above, to provide a blended naphtha. The olefinic naphtha may be made by processes as described herein.

The blended naphtha according to the present invention comprises less than 10 ppm sulfur and has an acid number of less than 1.5 mg KOH/g. Preferably, the blended naphtha has an acid number of less than 0.5 mg KOH/g. Also, preferably the blended naphtha also contains less than 10 ppm nitrogen, and more preferably both sulfur and nitrogen are less than 5 ppm, more preferably less than 2 ppm, and even more preferably less and 1 ppm. In addition, preferably the blended naphtha comprises less than 10 weight % aromatics, more preferably less than 5 weight % aromatics, and even more preferably less than 2 weight % aromatics.

The bended naphtha according to the present invention may comprise varying amounts of olefinic naphtha versus the other naphtha as defined above. Preferably, the olefinic naphtha comprises 10 to 90 weight % olefinic naphtha and 90 to 10 weight % other naphtha as defined above. More preferably a blended naphtha comprises 30 to 70 weight % olefinic naphtha and 70 to 30 weight % other naphtha.

The olefinic naphtha of the present invention provides a superior feed for a naphtha cracker for the production of lower olefins. The process for producing lower olefins according to the present invention comprises converting at least a portion of the olefinic naphtha, as described above, in a naphtha cracker to a product stream comprising lower olefins and lower olefins are recovered from this product stream.

Thermal cracking of hydrocarbons is the principal route for the industrial production of ethylene. Typical conditions for conducting thermal cracking to produce ethylene are described in K. M. Sundaram, et al., *Ethylene*, Kirk-Othmer Encyclopedia of Chemical Technology, Apr. 16, 2001, herein incorporated by reference in its entirety. The thermal cracking reaction proceeds in pyrolysis coils of a radiant section of a furnace. Since coke is also formed during pyrolysis, steam is added as a diluent to the feed. The steam minimizes the side reaction forming coke, and improves selectivity to produce the desired olefins by lowering hydrocarbon partial pressure. The temperature of the hydrocarbon and steam mixture entering the radiant chamber (known as the crossover temperature) is 500 to 700° C.

Depending on the residence time and required feed severity, the coil outlet temperature is typically maintained between 775 and 950° C.

The combination of low residence time and low partial pressure produces high selectivity to olefins at a constant feed conversion. In the 1960s, the residence time was 0.5 to 0.8 seconds, whereas in the late 1980s, residence time was typically 0.1 to 0.15 seconds. Typical pyrolysis heater characteristics are given in the below table.

TABLE

Pyrolysis Heater Characteritics

| Single heater characteristic | Range |
| --- | --- |
| number of coils | 2–176 |
| coil length, m | 9–80 |

TABLE-continued

Pyrolysis Heater Characteritics

| Single heater characteristic | Range |
|---|---|
| inside coil diameter, mm | 30–200 |
| process gas outlet temperature, °C. | 750–950 |
| clean coil metal temperature, °C. | 900–1,080 |
| max metal temperature, °C. | 1,040–1,150 |
| average heat absorption, kW/m² ext. are a | 50–110 |
| bulk residence time, s | 0.1–0.6 |
| coil outlet pressure, kPa[a] | 150–275 |
| clean coil pressure drop, kPa[a] | 10–200 |

[a]To convert kPa to bar, divide by 100.

Cracking reactions are endothermic, 1.6–2.8 MJ/kg (700–1200 BTU/1b) of hydrocarbon converted, with heat supplied by firing fuel gas and/or fuel oil in side-wall or floor burners.

Side-wall burners usually give uniform heat distribution, but the capacity of each burner is limited (0.1–1 MW) and hence 40 to 200 burners are required in a single furnace. With modern floor burners, also called hearth burners, uniform heat flux distribution can be obtained for coils as high as 10 m, and these are extensively used in newer designs. The capacity of these burners vary considerably (1–10 MW), and hence only a few burners are required. The selection of burners depends on the type of fuel (gas and/or liquid), source of combustion air (ambient, preheated, or gas turbine exhaust), and required $NO_x$ levels. The reaction mixture exiting the furnace is quickly cooled in quench coolers.

Using the olefinic naphtha, as described above, as the feed to a naphtha cracker increases the yields of ethylene in comparison to paraffinic naphtha. The improvement in yields of ethylene during naphtha cracking can be understood by examining the chemistry of naphtha cracking. For a typical $C_6$ paraffin, the cracking reaction (without dehydrogenation) is as follows:

$$C_6H_{14} \rightarrow 2C_2H_4 + C_2H_6$$

Accordingly, one mole of hexane gives two moles of ethylene and one mole of ethane.

The reaction for the corresponding $C_6$ olefin the reaction is as follows:

$$C_6H_{12} \rightarrow 3C_2H_4$$

Since the olefin is hydrogen deficient in comparison to the paraffin, less low-valued ethane is produced and the yield of desired ethylene potentially increases by 50%. However, under commercial conditions a portion of the starting hexane would be dehydrogenated to form hexene and hydrogen, thus increasing the actual yield of ethylene over what would be expected without dehydrogenation. Nevertheless, when olefinic feeds are used, ethylene yields are increased over what is observed with the corresponding paraffins. Accordingly, the cracking reaction of the present invention is more efficient since it uses an olefinic naphtha feed, as described above.

Furthermore, the cracking reaction of the present invention using an olefinic naphtha feed is more economical. While both conversions of paraffins (i.e., hexane) and olefins (i.e., hexene) to ethylene are endothermic and thus require high temperatures, the conversion of olefins is less endothermic than the conversion of paraffins because the endothermic dehydrogenation reaction does not occur to the same extent. Accordingly, thus energy consumption during conversion of olefinic naphtha to ethylene is lower than what would be expected for the corresponding paraffin. This lower energy consumption reduces the operating cost of the steam cracker.

It should be noted that current feedstocks used in naphtha crackers do not contain significant amounts of olefins because they are derived from petroleum, which is typically devoid of these compounds.

The processing of an olefinic feedstock in a naphtha cracker may result in an increase in the furnace tube coking rate. However, if this happens, any one or combinations of the following actions may be taken to control this problem. These actions include increasing the frequency of decoking operations, increasing the $H_2O$/hydrocarbon feedstock ratio, adding sulfur or a sulfur-containing stream to the feedstock, and coating the reactor with a coke passivation agent such as tin, chromium, aluminum, germanium, and combinations thereof.

In the process of the present invention for producing lower olefins, at least a portion of a hydrocarbon asset is converted to synthesis gas. The hydrocarbon asset may be selected from the group consisting of coal, natural gas, petroleum, and combinations thereof. At least a portion of the synthesis gas is converted to an olefinic naphtha by a Fischer-Tropsch process, as described above. The olefinic naphtha is isolated from the Fischer-Tropsch product stream and may be optionally purified by contacting with a metal oxide at elevated temperatures, also as described above. At least a portion of the olefinic naphtha is converted in a naphtha cracker to a product stream comprising lower olefins and at least a portion of the lower olefins are recovered from the product stream. Preferably, these lower olefins comprise ethylene.

Figure 1:
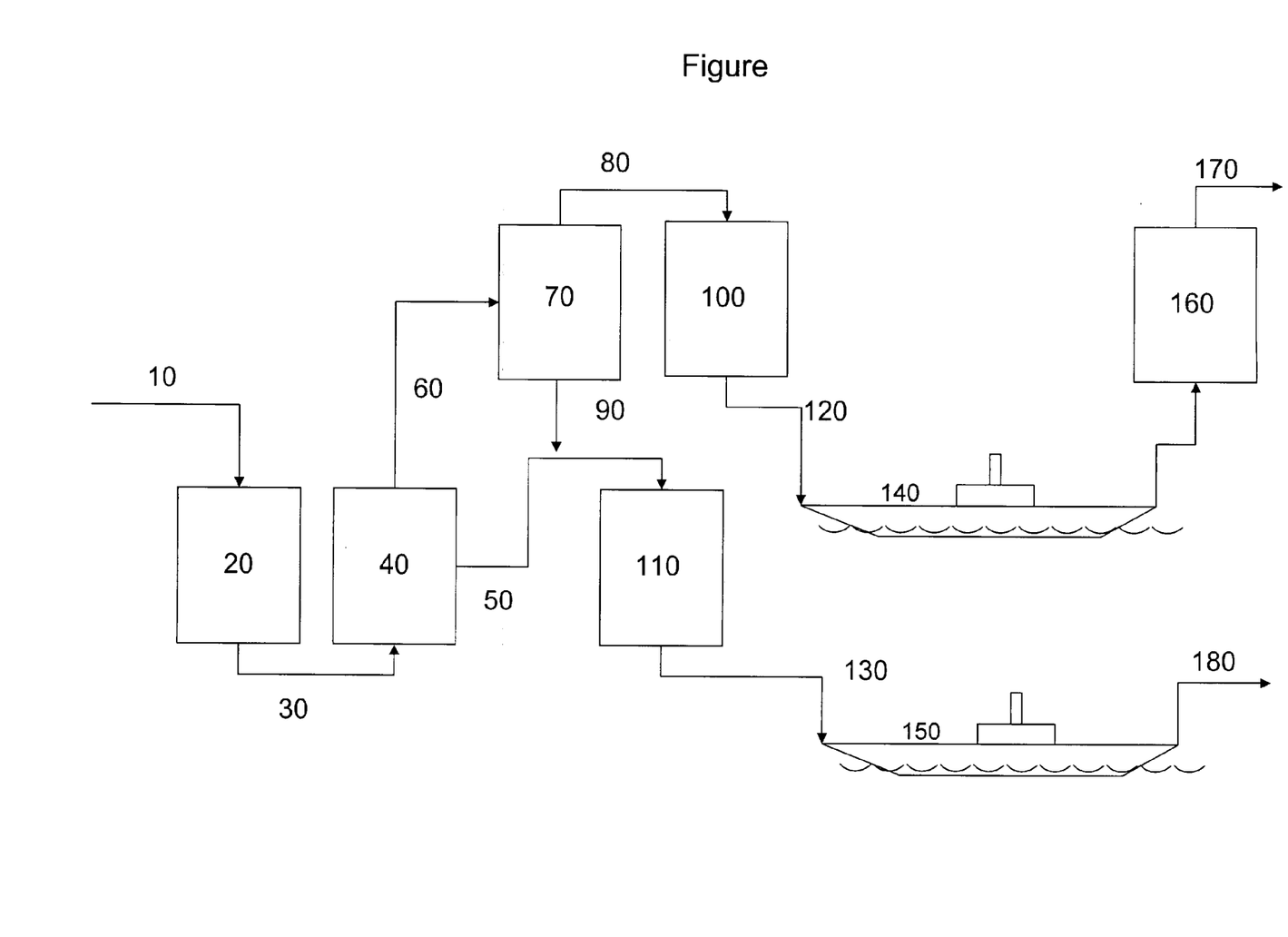
The FIGURE is an illustration of a process for converting natural gas to ethylene with co-production of other salable products.

A preferred embodiment of the present invention is illustrated in FIG. 1. In a location remote from the ethylene manufacturing plant, methane (10) is mixed with oxygen and steam (neither shown) and reacted in a synthesis gas generator (20) to form a synthesis gas stream (30). The synthesis gas is reacted in a slurry phase Fischer-Tropsch unit (40) to produce a liquid phase product (50) and a vapor phase product (60). The vapor phase product is separated to form a distillate range material (90) which contains $C_{10}$ and greater hydrocarbonaceous compounds. Also produced in this separation is an olefinic naphtha (80), which contains $C_5$ to 400° F. hydrocarbonaceous compounds. The olefinic naphtha is passed downflow through a purification unit (100) at 680° F., 50 psig, and 5 LHSV without added gaseous components. The purification unit contains alumina. The purification unit removes more than 80% of the oxygenated compounds, increases the olefin content, and reduces the acidity of the olefinic naphtha. A purified olefinic naphtha is produced (120) and shipped (140) to an ethylene manufacturing site where it is cracked in a naphtha cracker (160) to produce an ethylene containing stream (170). Salable, ethylene is recovered from the ethylene containing stream by steps not shown.

Meanwhile, the liquid phase product from the Fischer-Tropsch facility (50), which contains 400° F.+ material, is blended with the distillate range material (90) and the blend is processed in a hydrogenation facility (110) that converts the product into salable products: diesel fuel, jet fuel, and/or lubricating oil base stock (130). The hydrogenation facility consists of hydrocracking, hydrotreating, and/or hydroisomerization steps. These salable products are shipped (150) to markets (180). Alternatively, paraffinic naphtha (not shown) produced in the hydrogenation facility (110) along with other salable products can be blended with the purified olefinic naphtha (120) and shipped.

The optional purification treatment of the olefinic naphtha can be performed either before shipping (as shown above) or after shipping and prior to conversion in the steam cracker, or it can be performed at both locations.

EXAMPLES

The invention will be further explained by the following illustrative examples that are intended to be non-limiting.

Example 1

Fischer-Tropsch Olefinic Naphthas

Two olefinic naphthas prepared by the Fischer-Tropsch process were obtained. The first (Feedstock A) was prepared by use of a iron catalyst. The second (Feedstock B) was prepared by use of an cobalt catalyst. The Fischer-Tropsch process used to prepare both feeds was operated in the slurry phase. Properties of the two feeds are shown below in Table 4 to follow.

Feedstock A contains significant amounts of dissolved iron and is also acidic. It has a significantly poorer corrosion rating.

For purposes of this invention, Feedstock B is preferable. It contains fewer oxygenates, has a lower acid content, and is less corrosive. Thus it is preferable to prepare olefinic naphtha for use in ethylene production from cobalt catalysts rather than iron catalysts. Naphtha from cobalt catalysts may have low enough levels of impurities that the naphtha may be able to be used without further treatment or purification, as described above.

A modified version of ASTM D6550 (Standard Test Method for the Determination of the Olefin Content of Gasolines by Supercritical Fluid Chromatography—SFC) was used to determine the group types in the feedstocks and products. The modified method is to quantify the total amount of saturates, aromatics, oxygenates and olefins by making a 3-point calibration standard. Calibration standard solutions were prepared using the following compounds: undecane, toluene, n-octanol and dodecene. External standard method was used for quantification and the detection limit for aromatics and oxygenates is 0.1% wt and for olefins is 1.0% wt. Please refer to ASTM D6550 for instrument conditions.

A small aliquot of the fuel sample was injected onto a set of two chromatographic columns connected in series and transported using supercritical carbon dioxide as the mobile phase. The first column was packed with high surface area silica particles. The second column contained high surface area silica particles loaded with silver ions.

Two switching valves were used to direct the different classes of components through the chromatographic system to the detector. In a forward-flow mode, saturates (normal and branched alkanes and cyclic alkanes) pass through both columns to the detector, while the olefins are trapped on the silver-loaded column and the aromatics and oxygenates are retained on the silica column. Aromatic compounds and oxygenates were subsequently eluted from the silica column to the detector in a back flush mode. Finally, the olefins were back flushed from the silver-loaded column to the detector.

A flame ionization detector (FID) was used for quantification. Calibration was based on the area of the chromatographic signal of saturates, aromatics, oxygenates and olefins, relative to standard reference materials, which contain a known mass % of total saturates, aromatics, oxygenates and olefins as corrected for density. The total of all analyses was within 3% of 100% and normalized to 100% for convenience.

The weight percent olefins can also be calculated from the bromine number and the average molecular weight by use of the following formula:

Wt % Olefins=(Bromine No.)(Average Molecular Weight)/159.8.

It is preferable to measure the average molecular weight directly by appropriate methods, but it can also be estimated by correlations using the API gravity and mid-boiling point as described in "Prediction of Molecular Weight of Petroleum Fractions" A. G. Goossens, IEC Res. 1996, 35, p. 985–988.

Preferably the olefins and other components are measured by the modified SFC method as described above.

A GCMS analysis of the feedstocks determined that the saturates were almost exclusively n-paraffins, and the oxygenates were predominantly primary alcohols, and the olefins were predominantly primary linear olefins (alpha olefins).

Example 2

Dehydration Catalysts

Commercial Silica Alumina and Alumina extrudates were evaluated for dehydration of the Olefinic Naphthas. Properties of the extrudates are shown below in Table 1.

TABLE 1

| | Extrudate | |
| --- | --- | --- |
| Method of manufacture | Silica Alumina 89% silica alumina powder bound with 11% alumina | Alumina Alumina extrudate |
| Particle Density, gm/cm3 | 0.959 | 1.0445 |
| Skeletal Density, gm/cm3 | 2.837 | |
| BET Surface area, m2/g | 416 | 217 |
| Geometric Average pore size, Angstroms | 54 | 101 |
| Macropore volume, cc/g (1000 + Angstroms) | 0.1420 | 0.0032 |
| Total pore volume, cc/g | 0.636 | 0.669 |

Example 3

Dehydration over Silica Alumina

The dehydration experiments were performed in one inch downflow reactors without added gas or liquid recycle. The catalyst volume was 120 cc.

The Fe-based condensate (Feed A) was treated with the commercial silica alumina.

This catalyst was tested at 50 psig and temperature of 480° F., 580° F., and 680° F. with space velocity at one LHSV and three LHSV. At one LHSV, the total olefin content was 69–70% at all three temperatures, which indicated full conversion of the oxygenates. At 680° F. some cracking was observed by the light product yields: total C4- was 1.2% and C5–290° F. was 25% (vs. 20% in the feedstock). At three LHSV and 480° F. and 580° F. the total olefins were lower at 53–55%. High dehydration activity was obtained at 680° F. and three LHSV with total olefin content of 69%. GCMS data indicated that significant amount of 1-olefin was converted to internal or branched olefins. The total olefins at 480° F. was 69% initially but was 55% near the end of the test (~960 hours on stream). Significant amount of carbon was observed on the catalyst after unloading the catalyst. The catalyst apparently fouled.

TABLE 2

| Dehydration PP72-457, Si—Al catalyst | Temp, F | LHSV | Bromine method Bromine # | % Olefin | GC-MS Data Alpha-olefins Total olefins |
|---|---|---|---|---|---|
| Sample A | | | 50.6 | 51.6 | 90% |
| Product D | 680 | 3 | 71.7 | 70.3 | 5% |
| | 680 | 1 | 72.2 | 70.5 | 6% |

The detailed analysis of the product (D) from the test at 3 LHSC and 680° F. is shown below in Table 4.84% of the oxygen was removed, the corrosion rating was improved, and iron was reduced to below the level of detection. The acidity of the naphtha was reduced by 25%. The oxygenates were converted to olefins as shown by the increase in olefin content and the decrease in oxygenate content.

Example 4

Dehydration Over Alumina

The Co-based cold condensate (Feedstock B) was also treated as in Example 2, but with the alumina catalyst. Temperatures from 480° F. to 730° F. and LHSV values from one to five were explored. At high temperature and one LHSV, GCMS data indicated that the double bond isomerization was significant (reduced alpha-olefin content). At five LHSV and 580° F., dehydration conversion was significantly lower, and the majority of the olefins were primary linear olefins. This test ran 2000 hours with no indication of fouling.

These results show that it is possible to eliminate all the oxygenates from the sample and convert them to olefins. At high oxygenate removal levels, a significant portion of the alpha olefins are isomerized to internal olefins. Although internal olefins have less value than the alpha olefins as a feedstock for ethylene production, isomerization to internal olefins does not reduce the value below standard paraffinic naphtha or destroy any value for the feedstock.

Product (C) was prepared from operation at five LHSV and 680° F. Detailed properties are shown below in Table 1.87% of the oxygen is removed, the acidity was reduced by 55%, and the trace of iron in the sample was removed. The acidity of the final material was below 0.5 mg KOH/g, the typical maximum for petroleum crudes. The oxygenates were converted to olefins as shown by the increase in olefin content which approximately matched the decrease in oxygenate content.

TABLE 4

| | Experiment No. | | | |
|---|---|---|---|---|
| | 1 | 2 | 1 | 3 |
| | Feed/Product ID | | | |
| | Fe Cond. A | Product D | Co Cond. B | Product C |
| Process conditions | | | | |
| Catalyst | None | SiAl | None | Alumina |
| LHSV, h-1 | — | 3 | — | 5 |
| Temperature, F. | — | 680 | — | 680 |
| Pressure, psig | — | 50 | — | 50 |
| Run hours | — | 582–678 | — | 1026–1122 |
| API | 56.5 | 58.1 | 56.6 | 57.9 |
| Bromine No. | 50.6 | 71.7 | 21 | 27.6 |
| Average molecular weight | 163 | 157 | 183 | 184 |
| Wt % Olefin (calc. from Br2 No.) | 51.6 | 70.3 | 24 | 32 |
| KF Water, ppm wt | 494 | 58 | 530 | 57 |
| Oxygen by NAA, wt % | 1.61 | 0.26 | 0.95 | 0.12 |

TABLE 3

| Dehydration PP72-461461, alumina catalyst Sample ID | Temp, F | LHSV | SFC method Oxygenates, % wt | Bromine method Bromine# | % Olefin | GC-MS Data Alpha-olefins/Total olefins | C4- Gas Yields Wt % | Total Acid No. |
|---|---|---|---|---|---|---|---|---|
| Feed B: | | | 8.6 | 20.4 | 24.2 | 94% | | 0.86 |
| | 480 | 1 | 7.4 | 21.3 | 25.2 | 92% | 0.32 | |
| | 580 | 1 | 0.9 | 27.5 | 31.8 | 85% | <0.5 | |
| | 580 | 1 | 0.8 | 28.2 | 33.1 | 91% | 0.34 | 0.6 |
| | 580 | 1 | 0.9 | 27.1 | 31.1 | 93% | 0.36 | |
| | 580 | 2 | 1.3 | 27.1 | 31.3 | 86% | <0.5 | |
| | 580 | 3 | 2.1 | 26.5 | 30.6 | 86% | <0.5 | 0.48 |
| | 630 | 1 | 0.6 | 27.9 | 32.2 | 78% | 0.46 | 0.32 |
| | 630 | 2 | 0.8 | 28.1 | 32.4 | 79% | 0.38 | |
| | 630 | 3 | 0.8 | 29.4 | 33.9 | 86% | 0.24 | 0.63 |
| | 630 | 4 | 1.0 | 28.7 | 33.1 | 87% | 0.20 | |
| | 630 | 5 | 1.1 | 27.1 | 31.1 | 83% | 0.18 | 0.67 |
| | 680 | 1 | <0.1 | 31.1 | 35.6 | 4% | 0.51 | 0.06 |
| | 680 | 2 | 0.3 | 26.7 | 30.8 | 30% | 0.40 | 0.18 |
| | 680 | 3 | 0.5 | 26.5 | 30.6 | 71% | 0.33 | |
| | 680 | 3 | 0.6 | 26.9 | 31.1 | 78% | <0.5 | |
| | 680 | 4 | 0.6 | 27.6 | 32.0 | 76% | <0.5 | |
| | 680 | 4 | 0.6 | 29.1 | 33.3 | 73% | 0.20 | |
| | 680 | 5 | 0.7 | 28.1 | 32.3 | 78% | 0.18 | 0.39 |
| | 680 | 5 | 0.7 | 27.8 | 31.9 | 79% | <0.5 | |
| | 730 | 3 | 0.1 | 31.8 | 36.1 | 7% | 0.33 | 0.12 |

TABLE 4-continued

| | Experiment No. | | | |
|---|---|---|---|---|
| | 1 | 2 | 1 | 3 |
| | | Feed/Product ID | | |
| | Fe Cond. A | Product D | Co Cond. B | Product C |
| SFC Analysis, Wt % | | | | |
| Saturates | 33.5 | 35.1 | 67.4 | 68.0 |
| Aromatics | 1.2 | 1.5 | 0.3 | 0.4 |
| Olefins | 55.7 | 62.2 | 23.7 | 30.9 |
| Oxygenates | 9.6 | 1.2 | 8.6 | 0.7 |
| Acid Test | | | | |
| Total Acid, mg KOH/g | 3.17 | 2.33 | 0.86 | 0.39 |
| BUF EP, mg KOH/g | 3.10 | 2.30 | 0.84 | 0.35 |
| Cu Strip Corrosion | | | | |
| Rating | 2c | 2a | 1b | 1b |
| Sulfur, ppm wt | <1 | n/a | <1 | <1 |
| Nitrogen, ppm | 0.56 | n/a | 1.76 | 1.29 |
| ASTM D2887 Simulated Distillation by wt %, ° F. | | | | |
| 0.5 | 86 | 102 | 76 | 91 |
| 10 | 237 | 214 | 243 | 247 |
| 30 | 301 | 303 | 339 | 338 |
| 50 | 373 | 356 | 415 | 414 |
| 70 | 417 | 417 | 495 | 486 |
| 90 | 484 | 485 | 569 | 572 |
| 95 | 517 | 518 | 596 | 599 |
| 99.5 | 639 | 622 | 662 | 666 |
| Metals by ICP, ppm | | | | |
| Fe | 44.960 | 0.980 | 2.020 | <0.610 |
| Zn | 2.610 | <0.380 | <0.360 | <0.350 |

Metal elements below ICP limit of detection in all samples:
Al, B, Ba, Ca, Cr, Cu, K, Mg, Mo, Na, Ni, P, Pb, S, Si, Sn, Ti, V.

Example 5

Adsorption of Oxygenates

Trace levels of oxygenates not removed by the high temperature treatment can be removed by adsorption using sodium X zeolite (commercial 13X sieve from EM Science, Type 13X, 8–12 Mesh Beads, Part Number MX1583T-1).

The adsorption test was carried out in a up-flow fixed bed unit. The feed for the adsorption studies was produced by processing the Co condensate (Feed B) over alumina at 5 LHSV, 680° F. and 50 psig. The feed for the adsorption studies had acid number of 0.47 and oxygenate content by SFC of 0.6%.

Process conditions for the adsorption were: ambient pressure, room temperature, and 0.5 LHSV. The oxygenate content of the treated products was monitored by the SFC method. The adsorption experiment was continued until breakthrough—defined as the appearance of an oxygenate content of 0.1% or higher. The breakthrough occurred at when the sieve had adsorbed an equivalent amount of 14 wt % based on the feed and product oxygenates. The product after treatment showed 0.05 wt % oxygen by neutron activation, <0.1 ppm nitrogen, and total acid number of 0.09.

The adsorbent could be regenerated by known methods: oxidative combustion, calcinations in inert atmosphere, water washing, and the like, and in combinations.

These results demonstrate that adsorption processes can also be used for oxygenate removal. They can be used as such, or combined with dehydration.

Various modifications and alterations of this invention will become apparent to those skilled in the art without departing from the scope and spirit of this invention. Other objects and advantages will become apparent to those skilled in the art from a review of the preceding description.

That which is claimed is:

1. A process for producing lower olefins comprising:
    a. converting at least a portion of a hydrocarbon asset to synthesis gas;
    b. converting at least a portion of the synthesis gas to an olefinic naphtha by a Fischer-Tropsch process;
    c. converting at least a portion of the olefinic naphtha in a thermal naphtha cracker to a product stream comprising lower olefins; and,
    d. recovering at least a portion of the lower olefins from the product stream of the thermal naphtha cracker.

2. A process according to claim 1, wherein the olefinic naphtha has a total acid number of less than 1.5.

3. A process according to claim 1, further comprising the step of purifying the olefinic naphtha to reduce dissolved solids and acids therein to provide a purified naphtha.

4. A process according to claim 3, wherein the purified olefinic naphtha has a total acid number of less than 0.5.

5. A process according to claim 3, wherein the purifying step is performed by contacting the olefinic naphtha with a metal oxide at elevated temperatures.

6. A process according to claim 5, wherein the metal oxide is selected from the group consisting of alumina, silica, silica-alumina, zeolites, clays, and mixtures thereof.

7. A process according to claim 3, further comprising the step of separating water and carbon dioxide formed in the purifying step from the purified naphtha.

8. A process according to claim 1, wherein the olefinic naphtha comprises 10 to 80 weight percent olefins and 20 to 90 weight percent non-olefins, wherein the non-olefins comprise greater than 50 weight percent paraffins.

9. A process according to claim 1, wherein the olefinic naphtha comprises 50 to 80 weight percent olefins and 20 to 50 weight percent non-olefins, wherein the non-olefins comprise greater than 50 weight percent paraffins.

10. A process according to claim 1, wherein the olefinic naphtha comprises less than 5 weight percent aromatics, less than 5 ppm sulfur, and less than 5 ppm nitrogen.

11. A process according to claim 8, wherein the olefins of the olefinic naphtha comprise greater than 50 weight % linear primary olefins.

12. A process according to claim 8 wherein the olefins of the olefinic naphtha comprise greater than 80 weight % linear primary olefins.

13. A process according to claim 1, further comprising the step of blending the olefinic naphtha with a naphtha selected from the group consisting of a hydrotreated Fischer-Tropsch derived naphtha, a hydrocracked Fischer-Tropsch derived naphtha, a hydrotreated petroleum derived naphtha, a hydrocracked petroleum derived naphtha, and combinations thereof to provide a blended naphtha and converting a least a portion of the blended naphtha in the thermal naphtha cracker.

14. A process for producing ethylene comprising:
    a. converting at least a portion of a hydrocarbon asset to synthesis gas;
    b. converting at least a portion of the synthesis gas to a hydrocarbon stream in a Fischer-Tropsch process unit;

c. isolating an olefinic naphtha from the hydrocarbon stream, wherein the olefinic naphtha comprises 25 to 80 weight % olefins and 20 to 75 weight % non-olefins, wherein the non-olefins comprise greater than 75 weight % paraffins;

d. purifying the olefinic naphtha in the presence of a metal oxide to provide a purified olefinic naphtha having a total acid number of less than 1.5;

e. converting at least a portion of the purified olefinic naphtha in a thermal naphtha cracker to a product stream comprising ethylene; and f. recovering at least a portion of the ethylene from the product stream of the thermal naphtha cracker.

15. A process according to claim 14, wherein the olefins of the olefinic naphtha comprise greater than 50 weight % linear primary olefins, the non-olefins of the olefinic naphtha comprise greater than 90 weight % paraffins, and the paraffins have an i/n ratio of less than 1.

16. A process according to claim 14, wherein the purification step reduces the content of solids, acids, and alcohols in the olefinic naphtha.

17. A process according to claim 14, wherein the purified olefinic naphtha has a total acid number of less than 0.5.

18. A process according to claim 14, wherein the purification step is performed by passing the olefinic naphtha through a purification unit containing a metal oxide under conditions of 450 to 800° F., less than 1000 psig, and 0.25 to 10 LHSV without added gaseous components.

19. A process according to claim 14, wherein the metal oxide is selected from the group consisting of alumina, silica, silica-alumina, zeolites, clays, and mixtures thereof.

20. A process for manufacturing ethylene including a first site and a second site, remote from each other, wherein the first site forms an olefinic Fischer-Tropsch naphtha to be used at the second site, the second site forming the ethylene, wherein the process comprises:

a. receiving at the second site the olefinic Fischer-Tropsch naphtha, which is made by a process comprising:

i. converting a hydrocarbon asset to syngas;
  ii. subjecting the syngas to Fischer-Tropsch synthesis to form hydrocarbonaceous products;
  iii. isolating the olefinic Fischer-Tropsch naphtha from the hydrocarbonaceous products;

b. converting the olefinic naphtha in a thermal naphtha cracker to a product stream comprising ethylene; and c. isolating ethylene from the product stream of the thermal naphtha cracker.

21. A process according to claim 20, wherein the olefinic naphtha has a total acid number of less than 1.5.

22. A process according to claim 20, wherein the process to make the olefinic Fischer-Tropsch naphtha further comprises the step of purifying the olefinic naphtha to reduce the dissolved solids and acids therein to provide a purified naphtha.

23. A process according to claim 22, wherein the purified naphtha has a total acid number of less than 0.5.

24. A process according to claim 22, wherein the purifying is performed by contacting the olefinic naphtha with a metal oxide at elevated temperatures.

25. A process according to claim 24, wherein the metal oxide is selected from the group consisting of alumina, silica, silica-alumina, zeolites, clays, and mixtures thereof.

26. A process according to claim 20, wherein the olefinic naphtha comprises 50 to 80 weight percent olefins and 20 to 50 weight percent non-olefins, wherein the non-olefins comprise greater than 50 weight percent paraffins.

27. A process according to claim 20, further comprising the step of blending the olefinic naphtha with a naphtha selected from the group consisting of a hydrotreated Fischer-Tropsch derived naphtha, a hydrocracked Fischer-Tropsch derived naphtha, a hydrotreated petroleum derived naphtha, a hydrocracked petroleum derived naphtha, and combinations thereof to provide a blended naphtha and converting the blended naphtha in the thermal naphtha cracker.

* * * * *